(12) United States Patent
Hatlestad

(10) Patent No.: US 8,676,336 B2
(45) Date of Patent: *Mar. 18, 2014

(54) METHODS AND DEVICES FOR DETECTION OF CONTEXT WHEN ADDRESSING A MEDICAL CONDITION OF A PATIENT

(75) Inventor: John D. Hatlestad, Maplewood, MN (US)

(73) Assignee: Cardiac Pacemaker, Inc., St. Paul, MN (US)

( * ) Notice: Subject to any disclaimer, the term of this patent is extended or adjusted under 35 U.S.C. 154(b) by 34 days.

This patent is subject to a terminal disclaimer.

(21) Appl. No.: 13/188,956

(22) Filed: Jul. 22, 2011

(65) Prior Publication Data
US 2011/0275961 A1 Nov. 10, 2011

Related U.S. Application Data

(62) Division of application No. 12/171,210, filed on Jul. 10, 2008, now Pat. No. 7,986,998, which is a division of application No. 10/269,611, filed on Oct. 11, 2002, now Pat. No. 7,400,928.

(51) Int. Cl.
*A61B 5/04* (2006.01)

(52) U.S. Cl.
USPC .............................................. 607/60; 600/301

(58) Field of Classification Search
USPC .......................................................... 607/60
See application file for complete search history.

(56) References Cited

U.S. PATENT DOCUMENTS

| | | | |
|---|---|---|---|
| 4,860,751 A | 8/1989 | Callaghan | |
| 4,958,645 A | 9/1990 | Cadell et al. | |
| 4,993,421 A | 2/1991 | Thornton | |
| 5,025,791 A | 6/1991 | Niwa | |
| 5,193,535 A | 3/1993 | Bardy et al. | |
| 5,257,621 A | 11/1993 | Bardy et al. | |
| 5,284,491 A | 2/1994 | Sutton et al. | |
| 5,354,317 A | 10/1994 | Alt | |
| 5,458,123 A | 10/1995 | Unger | |
| 5,469,861 A | 11/1995 | Piscopo et al. | |
| 5,472,453 A | 12/1995 | Alt | |

(Continued)

FOREIGN PATENT DOCUMENTS

WO WO-0004945 A2 2/2000

OTHER PUBLICATIONS

"U.S. Appl. No. 10/269,611, Non-Final Office Action mailed Aug. 24, 2007", 12 pgs.

(Continued)

*Primary Examiner* — Eric D. Bertram
(74) *Attorney, Agent, or Firm* — Schwegman Lundberg & Woessner, P.A.

(57) ABSTRACT

Methods and devices detect context related to a patient when monitoring a physiological condition of the patient and/or when applying one or more modes of therapy. The context may be a patient context such as posture or an environmental context such as ambient conditions. The context may be used in various ways in relation to the physiological measurement, such as to control when the physiological measurements are made, to appropriately flag physiological measurements, to be recorded in association with the physiological measurements, and/or to correct the physiological measurements based on a reference context. A device such as a beacon transmitter is used in detecting the context and a measurement device such as an implantable cardiovascular device is used to capture the physiological measurements.

20 Claims, 6 Drawing Sheets

(56) References Cited

U.S. PATENT DOCUMENTS

| | | |
|---|---|---|
| 5,535,752 A | 7/1996 | Halperin et al. |
| 5,593,431 A | 1/1997 | Sheldon |
| 5,630,834 A | 5/1997 | Bardy |
| 5,704,352 A | 1/1998 | Tremblay et al. |
| 5,833,603 A | 11/1998 | Kovacs et al. |
| 5,865,760 A | 2/1999 | Lidman et al. |
| 5,904,708 A | 5/1999 | Goedeke |
| 5,957,957 A | 9/1999 | Sheldon |
| 5,987,352 A | 11/1999 | Klein et al. |
| 6,002,963 A | 12/1999 | Mouchawar et al. |
| 6,024,704 A | 2/2000 | Meador et al. |
| 6,044,297 A | 3/2000 | Sheldon et al. |
| 6,078,834 A | 6/2000 | Lurie et al. |
| 6,104,929 A | 8/2000 | Josse et al. |
| 6,104,949 A | 8/2000 | Pitts Crick et al. |
| 6,135,970 A | 10/2000 | Kadhiresan et al. |
| 6,203,495 B1 | 3/2001 | Bardy |
| 6,221,011 B1 | 4/2001 | Bardy |
| 6,240,316 B1 | 5/2001 | Richmond et al. |
| 6,261,230 B1 | 7/2001 | Bardy |
| 6,270,457 B1 | 8/2001 | Bardy |
| 6,277,072 B1 | 8/2001 | Bardy |
| 6,280,380 B1 | 8/2001 | Bardy |
| 6,312,378 B1 | 11/2001 | Bardy |
| 6,331,160 B1 | 12/2001 | Bardy |
| 6,334,063 B1 | 12/2001 | Charlier et al. |
| 6,336,903 B1 | 1/2002 | Bardy |
| 6,358,203 B2 | 3/2002 | Bardy |
| 6,368,284 B1 | 4/2002 | Bardy |
| 6,398,728 B1 | 6/2002 | Bardy |
| 6,411,840 B1 | 6/2002 | Bardy |
| 6,440,066 B1 | 8/2002 | Bardy |
| 6,473,652 B1 | 10/2002 | Sarwal et al. |
| 6,478,737 B2 | 11/2002 | Bardy |
| 6,517,481 B2 | 2/2003 | Hoek et al. |
| 6,607,485 B2 | 8/2003 | Bardy |
| 6,616,607 B2 | 9/2003 | Hashimoto et al. |
| 6,625,492 B2 | 9/2003 | Florio et al. |
| 6,647,295 B2 | 11/2003 | Florio et al. |
| 6,658,292 B2 | 12/2003 | Kroll et al. |
| 6,658,297 B2 | 12/2003 | Loeb |
| 6,662,047 B2 | 12/2003 | Sorensen et al. |
| 6,671,547 B2 | 12/2003 | Lyster et al. |
| 6,682,480 B1 | 1/2004 | Habib et al. |
| 6,692,446 B2 | 2/2004 | Hoek |
| 6,694,186 B2 | 2/2004 | Bardy |
| 6,704,595 B2 | 3/2004 | Bardy |
| 6,705,991 B2 | 3/2004 | Bardy |
| 6,738,671 B2 | 5/2004 | Christophersom et al. |
| 6,754,528 B2 | 6/2004 | Bardy et al. |
| 6,811,537 B2 | 11/2004 | Bardy |
| 6,826,425 B2 | 11/2004 | Bardy |
| 6,827,690 B2 | 12/2004 | Bardy |
| 6,834,203 B2 | 12/2004 | Bardy |
| 6,852,080 B2 | 2/2005 | Bardy |
| 6,866,629 B2 | 3/2005 | Bardy |
| 6,887,201 B2 | 5/2005 | Bardy |
| 6,893,397 B2 | 5/2005 | Bardy |
| 6,904,312 B2 | 6/2005 | Bardy |
| 6,907,288 B2 | 6/2005 | Daum |
| 6,908,437 B2 | 6/2005 | Bardy |
| 6,913,577 B2 | 7/2005 | Bardy |
| 6,926,668 B2 | 8/2005 | Bardy |
| 6,945,934 B2 | 9/2005 | Bardy |
| 6,951,539 B2 | 10/2005 | Bardy |
| 6,960,167 B2 | 11/2005 | Bardy |
| 6,974,413 B2 | 12/2005 | Bardy |
| 6,975,904 B1 * | 12/2005 | Sloman ........................... 607/28 |
| 6,978,182 B2 | 12/2005 | Mazar et al. |
| 6,997,873 B2 | 2/2006 | Bardy |
| 7,117,028 B2 | 10/2006 | Bardy |
| 7,384,395 B2 | 6/2008 | Hatlestsad et al. |
| 7,400,928 B2 | 7/2008 | Hatlestad |
| 7,986,998 B2 * | 7/2011 | Hatlestad ........................ 607/60 |
| 2001/0011153 A1 | 8/2001 | Bardy |
| 2002/0004670 A1 | 1/2002 | Florio et al. |
| 2002/0091326 A1 | 7/2002 | Hashimoto et al. |
| 2002/0169367 A1 | 11/2002 | Bardy |
| 2003/0144595 A1 * | 7/2003 | Lade ............................. 600/485 |
| 2003/0195397 A1 | 10/2003 | Bardy |
| 2004/0039263 A1 | 2/2004 | Bardy |
| 2004/0073093 A1 | 4/2004 | Hatlestad |
| 2004/0147979 A1 | 7/2004 | Bardy |
| 2004/0230127 A1 | 11/2004 | Bardy |
| 2004/0236237 A1 | 11/2004 | Bardy |
| 2004/0254613 A1 | 12/2004 | Ostroff et al. |
| 2005/0027331 A1 | 2/2005 | Bardy |
| 2005/0145246 A1 | 7/2005 | Hartley et al. |
| 2005/0154267 A1 | 7/2005 | Bardy |
| 2005/0165286 A1 | 7/2005 | Bardy |
| 2005/0171411 A1 | 8/2005 | KenKnight et al. |
| 2005/0182308 A1 | 8/2005 | Bardy |
| 2005/0192505 A1 | 9/2005 | Ostroff et al. |
| 2005/0234352 A1 | 10/2005 | Bardy |
| 2006/0241513 A1 | 10/2006 | Hatlestad et al. |
| 2007/0129641 A1 | 6/2007 | Sweeney |
| 2008/0082001 A1 | 4/2008 | Hatlestad et al. |

OTHER PUBLICATIONS

"U.S. Appl. No. 10/269,611, Notice of Allowance mailed Mar. 11, 2008", 7 pgs.

"U.S. Appl. No. 10/269,611, Response filed Nov. 21, 2007 to Non-Final Office Action mailed Aug. 24, 2007", 11 pgs.

"U.S. Appl. No. 11/291,479, Final Office Action mailed Feb. 2, 2010", 9 pgs.

"U.S. Appl. No. 11/291,479, Final Office Action mailed Nov. 13, 2008", 8 pgs.

"U.S. Appl. No. 11/291,479, Non-Final Office Action mailed Feb. 19, 2008", 8 pgs.

"U.S. Appl. No. 11/291,479, Non-Final Office Action mailed May 26, 2009", 8 pgs.

"U.S. Appl. No. 11/291,479, Non-Final Office Action Mailed Jul. 25, 2007", 10 pgs.

"U.S. Appl. No. 11/291,479, Response filed Jul. 21, 2008 to Non-Final Office Action mailed Feb. 19, 2008", 8 pgs.

"U.S. Appl. No. 11/291,479, Response filed Oct. 26, 2009 to Non-Final Office Action mailed May 26, 2009", 10 pgs.

"U.S. Appl. No. 11/291,479, Response filed Nov. 21, 2007 to Non-Final Office Action mailed Jul. 25, 2007", 8 pgs.

"U.S. Appl. No. 11/291,479, Response filed Mar. 4, 2009 to Final Office Action mailed Nov. 13, 2008", 10 pgs.

"U.S. Appl. No. 12/171,210 Non-Final Office Action mailed Aug. 6, 2010", 9 pgs.

"U.S. Appl. No. 12/171,210, Notice of Allowance mailed Mar. 21, 2011", 5 pgs.

"U.S. Appl. No. 12/171,210, Response filed Jan. 5, 2011 to Non-Final Office Action mailed Aug. 6, 2010", 13 pgs.

US 6,527,714, 03/2003, Bardy (withdrawn)

* cited by examiner

METHODS AND DEVICES FOR DETECTION OF CONTEXT WHEN ADDRESSING A MEDICAL CONDITION OF A PATIENT

RELATED APPLICATIONS

This application is a Divisional of U.S. application Ser. No. 12/171,210, filed Jul. 10, 2008, entitled "Methods and Device for Detection of Context when Addressing a Medical Condition of a Patient," now issued as U.S. Pat. No. 7,986,998, which is a Divisional of U.S. application Ser. No. 10/269,611, filed Oct. 11, 2002, entitled "Methods and Device for Detection of Context when Addressing a Medical Condition of a Patient," now issued as U.S. Pat. No. 7,400,928, which are incorporated herein by reference.

TECHNICAL FIELD

The present invention relates to monitoring physiological conditions and/or treating a medical condition of a patient. More specifically, the present invention relates to detecting a context that is related to the physiological condition and/or treatment of the patient.

BACKGROUND

Physiological conditions of a patient may be monitored either during visits to a physician or through frequent self-examinations by the patient. Although the health of the patient may be determinable from these monitoring sessions, certain health issues may not be readily apparent from such periodic monitoring. Additionally, periodic monitoring through self-examination and visits to a physician can be an inconvenience to the patient.

Medical devices that are coupled to the patient either periodically or constantly, as in the case of an implant, address many of these issues. The patient is not encumbered by the manual self-examination and is not required to make frequent visits to a physician. Instead, the medical device automatically makes measurements of a physiological condition of the patient, such as pulse or respiration rate, and stores the information for later retrieval or streams the data to another device or communication network. Thus, the physiological condition of the patient can be automatically monitored at anytime during which the medical device is coupled to the patient, regardless of context.

However, context may temporarily affect the physiological condition of the patient being monitored. Context can be divided into both a patient context and an environmental context. The patient context is a body-related factor, such as the posture, activity level, or mental/emotional state of the patient, and the patient context can cause the physiological condition of the patient to vary to a substantial degree. The environmental context is an external factor such as the ambient temperature or sound level and can also cause the physiological condition to vary.

The context is typically unknown when the medical device is making the physiological measurements, and therefore any deviations from normal values for a physiological condition may be the result of context rather than a health condition of the patient. Therefore, the physiological measurements being made regardless of context cannot be relied upon with a high degree of certainty when assessing the health of the patient since the unknown context may skew the measurements.

Additionally, the context may be relevant to the type of therapy that is being provided to a patient. For example, for certain contexts the patient may be better served by a particular mode of therapy from a medical device, such as immediate defibrillator shocks while driving upon detection of fibrillation. For other contexts, the patient may be better served by a different mode of therapy from the medical device, such as taking more time to more accurately determine the patient's condition before administering defibrillator shocks. However, because the context is typically unknown, the medical device administers the defibrillator shocks without regard for the context surrounding the patient at any given time.

SUMMARY

Embodiments of the present invention address these problems and others by detecting the context when monitoring the physiological condition of the patient and/or when providing therapy to the patient. Thus, a particular context may be used in various ways in relation to the measurements of physiological condition and/or in relation to the type of therapy to be provided at any given time. For example, context may be used to control when the measurement of physiological conditions occurs, may be used to flag the measurements that occur, may be recorded in association with the physiological condition, or may be used to correct the measurements of the physiological condition according to a reference context. Similarly, the context may be used to determine when to provide a particular mode of therapy to a patient to address a medical condition.

One embodiment of the present invention involves utilizing a device to detect whether at least one contextual condition associated with the patient exists. When the existence of the at least one contextual condition is detected, the at least one physiological condition of the patient is automatically measured using a measurement device coupled to the patient.

Another embodiment involves measuring at least one physiological condition of the patient with a measurement device. While measuring the at least one physiological condition, an external device is utilized to detect whether at least one contextual condition associated with the patient exists. The measurements resulting from the measuring done while the at least one contextual condition continues to exist are flagged.

Another embodiment involves measuring at least one physiological condition of the patient using a measurement device. An external device is utilized to measure at least one condition defining a patient context. The measurements of the at least one physiological condition are correlated with the measurements of the at least one condition defining the patient context.

Another embodiment provides therapy to a patient. This embodiment involves utilizing a device to detect whether the patient is within a predefined proximity. When the patient is within the predefined proximity, a first mode of therapy is provided to the patient with a medical device.

Another embodiment also involves providing therapy to a patient. This embodiment involves utilizing a device to detect whether at least one contextual condition associated with the patient exists. A first mode of therapy is provided to the patient from a medical device while the at least one contextual condition continues to exists.

DETAILED DESCRIPTION

Embodiments of the present invention detect the context that exists when measurements of physiological conditions of the patient are measured and/or when one or modes of therapy are applied to the patient. The context may be correlated with the physiological measurements in various ways so that the context from one set of measurements to the next does not influence the physiological measurements and their value in assessing the health of the patient and the control of therapy to the patient.

Figure 1:
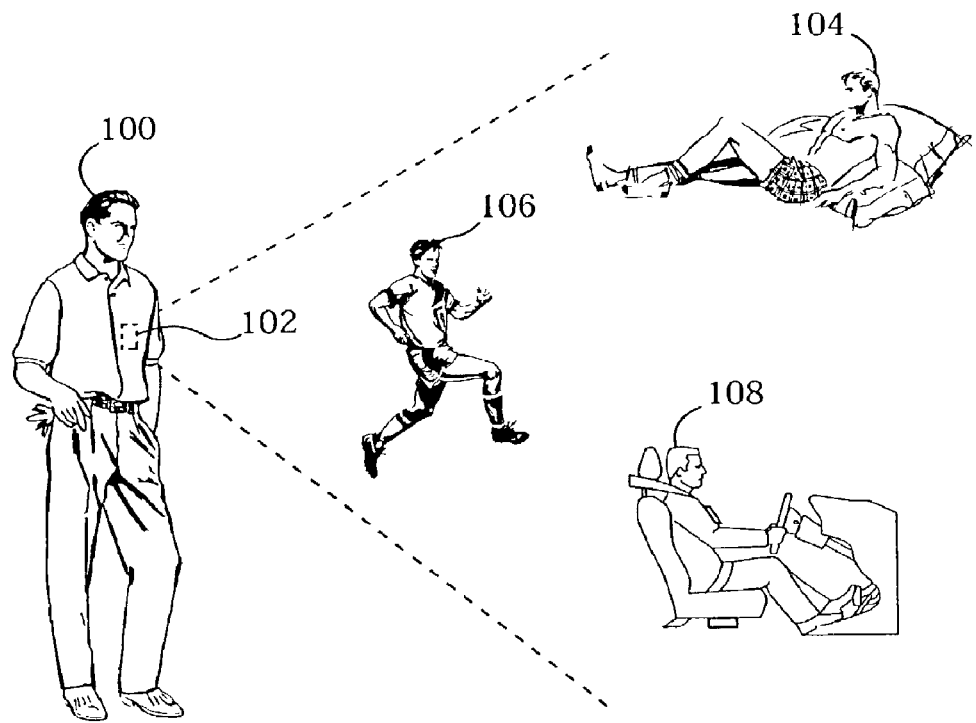
FIG. 1 shows a patient to be monitored and examples of the various patient contexts that may exist during physiological measurements and/or therapy delivery.

As shown in FIG. 1, a patient 100 may be monitored and/or treated periodically or continuously by a measurement device 102 that is coupled to the body of the patient 100. The patient 100 may experience various contextual conditions including various patient contexts and environmental contexts. As shown in FIG. 1, examples of patient contexts include a sleeping or lying down context 104, a running context 106, and a driving context 108. Each of these different patient contexts may affect the physiological condition being monitored in various ways. For example, pulse rate may be monitored and may decrease relative to a baseline level in sleeping context 104 but be increased relative to the baseline level in the running context 106 or driving context 108. Likewise, the patient context at any given time may be relevant to the mode of therapy to be applied to the patient.

To increase the value of the physiological measurements taken for the patient 100, it is desirable to correlate the context with the physiological measurements. The correlation may be brought about by detecting context and only taking measurements of the physiological condition when the context is as expected. Doing so provides a repeatable baseline for the measurements so that one set of measurements may be compared to the next or to known normal values to determine trends or deviations from normal values that indicate a health problem. Correlation may be brought about by detecting the context and flagging the measurements that are taken so that those taken during a particular context are flagged and may be used as the repeatable baseline, or conversely, not considered. Correlation may also be brought about by logging the context with the physiological measurements so that context may be considered upon reviewing the measurements. Additionally, context may be used to determine a correction for the measurements to normalize the measurements according to a baseline context.

To increase the effectiveness, safety, or other concern for therapy being provided to the patient 100, it is also desirable to determine the context when deciding what mode of therapy should be applied. One patient context may dictate that a particular mode of therapy not be used. For example, a mode of therapy may provide defibrillator shocks immediately upon detection of an abnormal rhythm, but such a form of therapy may be unsafe and/or unnecessarily uncomfortable for the patient because initial signs of fibrillation may not always call for defibrillator shocks. Therefore, when time is available, a proper mode of therapy may be to analyze over a relatively longer period of time the potential fibrillation condition of the patient to make a more accurate decision about the need for defibrillation. However, under other contexts such as while the patient is driving a car, it may be more appropriate to immediately administer the defibrillator shock upon initial detection of fibrillation to prevent the patient from losing consciousness. Thus, detecting the context allows a most appropriate mode of therapy to be chosen.

Figure 2:
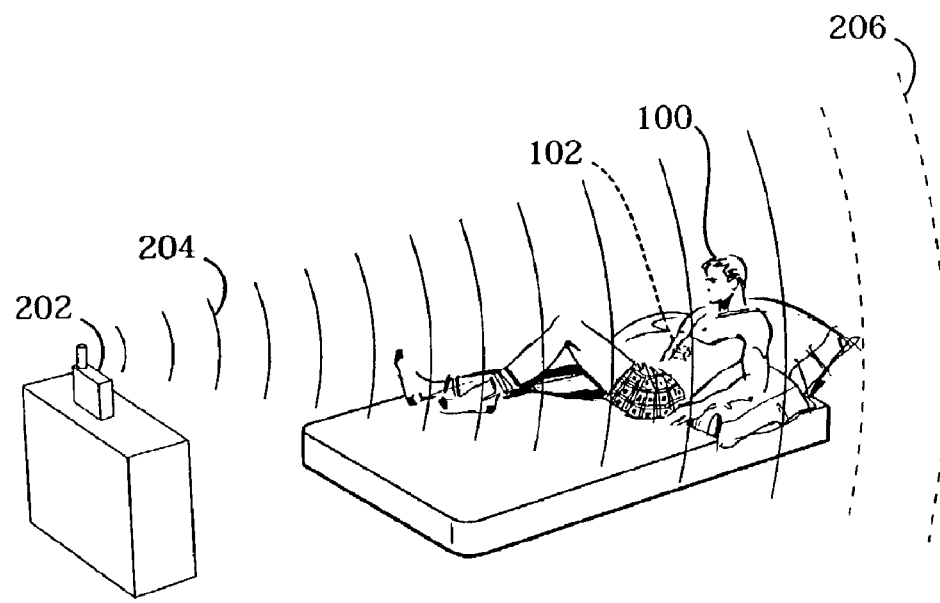
FIG. 2 shows an example of a patient being monitored and/or treated with a mode of therapy while a patient context is being detected through proximity sensing.

FIG. 2 shows one example of context detection. In this example, patient context is detected by proximity sensing. The patient 100 is lying down in bed and this position likely affects various physiological conditions of the patient that may be measured and may also dictate the mode of therapy to be provided. A measurement device 102 such as an implantable medical device is coupled to the patient 100. An external device 202, such as a beacon transmitter is positioned nearby the bed of the patient. When the patient lies down in bed, the measurement device 102 becomes within transmission range of the beacon transmitter 202. Upon receiving the transmitted signal 204 defining the transmission range, the measurement device behaves so as to allow correlation of the physiological measurements with the context of lying down. Upon the measurement device 102 moving out of range wherein the signal 206 is too weak, the measurement device 102 may behave differently because the detection of context has indicated a change. The patient can no longer be lying down in bed once the signal 204 is out of range. Likewise, one mode of therapy may be provided to the patient 100 when in the beacon signal 204 is received while another mode is provided otherwise.

As an example of how the measurement device 102 may respond to the detection of context, the measurement device 102 may begin taking measurements of a physiological condition such as pulse rate once the measurement device 102 is in range of the transmitter 202. Alternatively, the measurement device 102 can flag data as being recorded during an appropriate patient context so that the data is acceptable. As another alternative, the measurement device 102 can log the particular patient context being experienced with the measurement data, such as where the transmission signal 204 provides an ID of the transmitter 202 to the measurement device 102. In this scenario, multiple transmitters may be used to provide information regarding multiple patient contexts such as one for sleeping and one for driving. As another alternative, the measurement device 102 may employ algorithms to normalize or correct the measurements to correspond to those taken during a baseline context different than the present patient context. This may be done by applying correction factors associated with the present patient context (e.g., multiply pulse rate by a factor of 1.3 when pulse rate is recorded while the patient is lying down to approximate upright and awake pulse rate).

Figure 3:
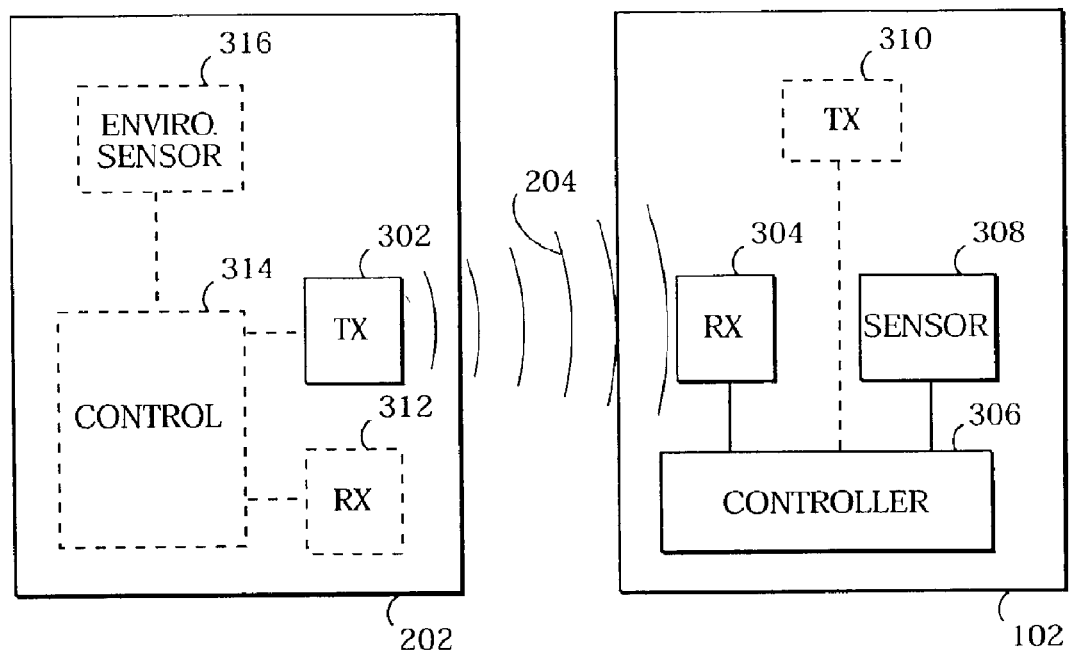
FIG. 3 is a block diagram of the major components of embodiments of devices of a first illustrative system for detecting context when measuring physiological conditions of the patient or providing a mode of therapy to the patient.

FIG. 3 shows the major components of a system for detecting context when making measurements of physiological conditions and/or when applying one or more modes of therapy to a patient. The system includes the external device 202 and the measurement device 102. The external device 202 includes a transmitter 302 that produces the signals received by the measurement device 102 when in range. The transmitter 302 typically outputs radio frequency electromagnetic signals that have a range that may be controlled based upon the power output of the transmitter 302, which may be user adjustable to adapt to various situations. The external device 202 can include various other features in addition to the transmitter 302 if additional functionality is desired.

For example, the external device may include a control circuit 314 that is operatively coupled to the transmitter 302 to turn the transmitter on and off according to one or more parameters. For example, it may be desirable to transmit the signal to the measurement device 102 to initiate measurements or a certain mode of therapy only during certain times of day and the controller 314 turns the transmitter 302 on and off according to the time of day. Thus, the time of day controls the measurements of physiological condition or the mode of therapy by the measurement device 102 in addition to the patient context. Environmental sensors 316 that are operatively coupled to the controller 314 may also be included so that the controller 314 turns the transmitter 302 on and off according to ambient conditions such as temperature or humidity that define an environmental context. Thus, the environmental context can control the measurements of physiological condition and/or the mode of therapy by the measurement device 102 in addition to the patient context.

The external device 202 may also include a receiver 312 operatively coupled to the controller 314. The receiver 312 can be used to receive information from the measurement device 102 for embodiments of the measurement device 102 that include a transmitter. As one example, the measurement device 102 may transmit the measurements of the physiological condition either in real time or after some period of storage to the receiver 312. The receiver 312 then passes the data to the controller 314 that may also act as a data logger to store the data in memory or pass it through a network connection. The data controller 314 may add the environmental context taken from the environmental sensor 316 to storage in association with the measurement data, and may add the patient context established by the external device 202, such as the sleeping context, to storage as well.

The measurement device 102 includes a detector such as receiver 304 that is coupled to a controller 306 and that signals to the controller 306 when the signal from the external device 202 is in range. Upon receiving the signal from the receiver 304, the controller 306 begins the activity that permits correlation of the patient context to the measurements of the physiological condition, such as beginning taking the measurements or flagging the measurements that are taken from that point forward. Additionally, or alternatively, the controller 306 may choose the mode of therapy to apply upon receiving the signal from receiver 304. A sensor 308 is operatively coupled to the controller 306 so that the measurements acquired by the sensor 308 may be passed to the controller to be stored in memory or transmitted to the external device 202 if the measurement device 102 is equipped with a transmitter 310 in communication with the controller 306.

The sensor 308 may be of various forms to capture the desired physiological conditions of the patient. For example, the measurement device 102 may be an implantable medical device such as a pacemaker that includes leads and circuitry forming a sensor that measures electrical activity of the heart such as the QRS complex, pulse rate, or atrioventricular delay. Other sensors are also applicable, such as an internal or external blood pressure or body temperature sensor.

Although the device 202 is shown as being an external device used to detect proximity to define a patient context, other forms of devices for use in detecting context in conjunction with a measurement device 102 may be used as well. For example, a detector device such as a tilt switch (not shown) may be included within the measurement device 102 to capture the tilt of the patient's body and can trigger the controller 306 to respond in a particular way in place of the receiver 304 triggering the controller 306. For example, the tilt switch may cause the controller 306 to begin taking measurements through the sensor 308 of a particular physiological condition only when the patient has become recumbent as determined from the output of the tilt switch. Additionally or alternatively, the tilt switch may cause the controller 306 to choose a particular mode of therapy when the patient has become recumbent as opposed to upright.

Figure 4:
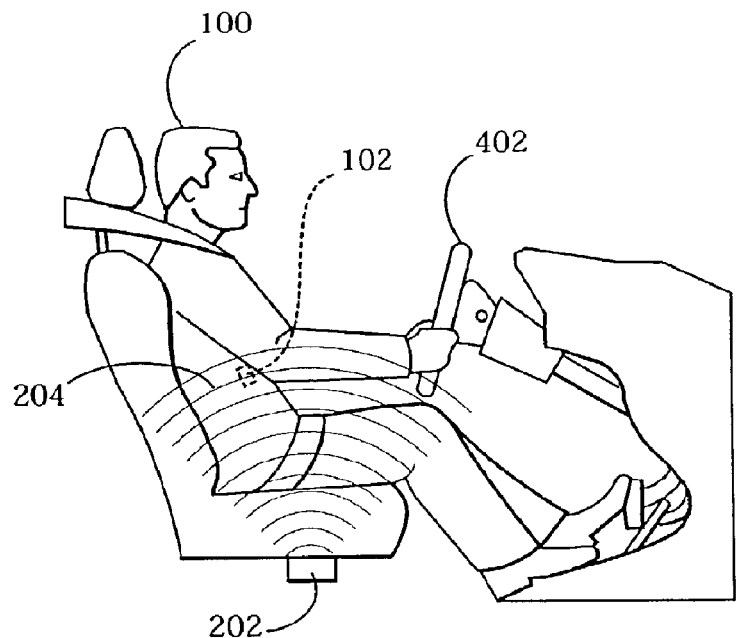
FIG. 4 shows another example of a patient being monitored or provided a mode of therapy while a patient context is being detected through proximity sensing.

Additionally, other situations may utilize proximity sensing to determine the patient context. For example, in FIG. 4 the patient 100 is driving a car by interacting with various controls 402 of the car. The external device 202 is placed proximal to the seat of the driver and outputs a signal 204 such as when the car is running by receiving power from a switched power connection of the automobile. The measurement device 102 is coupled to the patient 100 and becomes within range of the signals 204 once the patient 100 sits in the driver's seat. Therefore, upon beginning operation of the car, the external device 202 sends the signal 204 that causes the measurement device 102 to respond in a particular manner, such as by beginning measurement of a physiological condition or flagging the measurements being made as occurring during the new patient context. Additionally or alternatively, the device 102 may begin application of a particular mode of therapy suited for a patient driving a car when receiving the signal 204 of FIG. 4.

Figure 5:
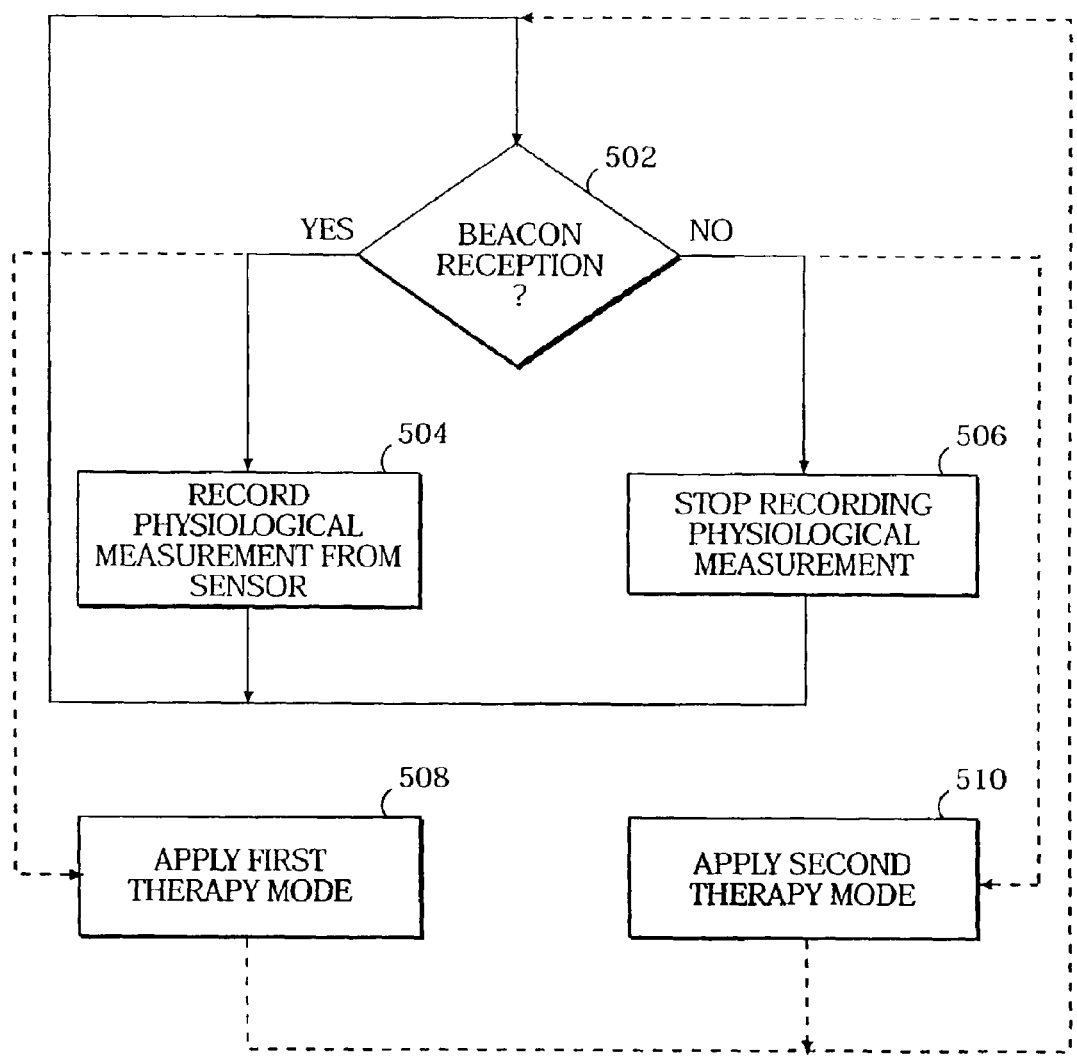
FIG. 5 shows an embodiment of the logical operations of an illustrative system for detecting patient context to start and stop the measurements of physiological conditions and/or to switch between first and second modes of therapy.

FIG. 5 provides an example of logical operations that may be performed by a measurement device 102 to detect and respond to a particular context to correlate the detected context with the measurement of physiological conditions and/or to apply a particular mode of therapy. As shown, the context is a patient context detected through proximity to a beacon transmitter 202 such as the situation shown in FIG. 2. The controller 306 of the measurement device 102 continuously or periodically polls the output of the receiver 304 to determine whether the beacon signal 204 has been received at query operation 502. If the beacon has been received, then the controller 306 begins recording to memory the physiological measurements taken from the sensor 308 at record operation 504 and/or begins applying a first mode of therapy at therapy operation 508. Additionally or alternatively, the controller 306 may begin outputting the measurements through the transmitter 310 to the external device 202 or another device that receives and records data to memory. Upon query operation 502 detecting that the beacon is not being received, then the recording of the physiological measurements stops at stop operation 506. Additionally or alternatively, once query operation detects that the beacon is not being received, a second mode of therapy begins in at therapy operation 510.

Figure 6:
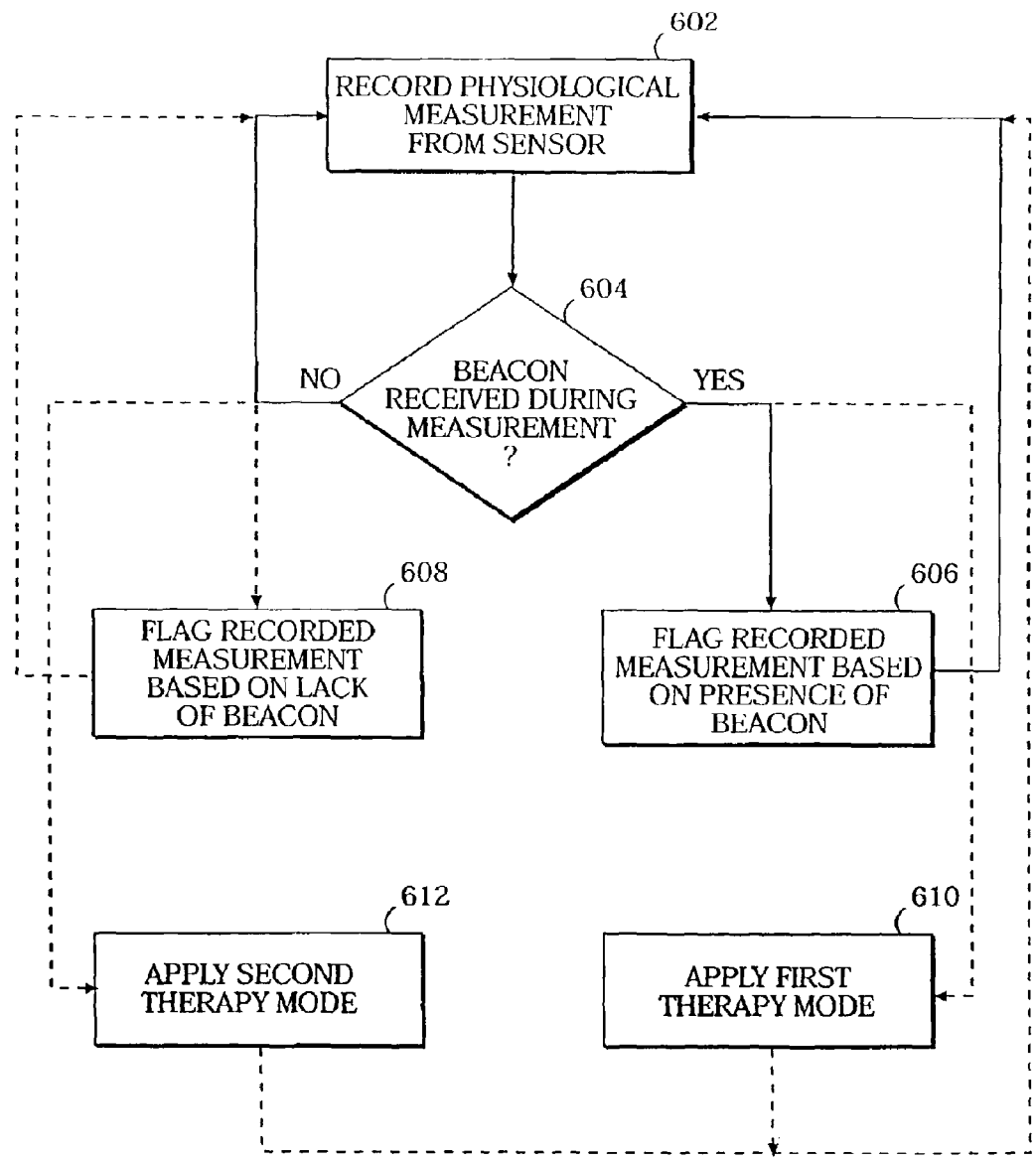
FIG. 6 shows another embodiment of the logical operations of an illustrative system for detecting patient context to flag the measurements of physiological conditions and/or to switch between first and second modes of therapy.

FIG. 6 shows another example of the logical operations of a measurement device 102 detecting a context and responding accordingly. These operations also apply to the situation of FIG. 2 where the patient context is set forth by proximity of the patient 100. The operations begin at record operation 602 where the controller 306 records the measurements received from the sensor 308. At query operation 604, the controller 306 detects whether the beacon signal 204 is received during the time the measurements are being recorded. If not, then the controller 306 continues to record the physiological measurements at record operation 602. Alternatively, the controller 306 begins flagging the measurements with an indicator based on the lack of beacon reception at flag operation 608. Additionally or alternatively, the controller 306 begins application of a second mode of therapy at therapy operation 612.

When query operation 604 does detect that the beacon signal 204 is received, then the controller 306 begins flagging the recorded measurements with an indicator based on the presence of beacon reception at flag operation 606. Additionally or alternatively, the controller 306 begins application of a first mode of therapy at therapy operation 610 in response to the beacon being received. The first and second modes of therapy may also rely upon the physiological measurements being made at record operation 602 to control therapy as necessary to address the medical condition of the patient 100, such as speeding up or slowing down the pulse rate based on the current pulse rate being recorded as well as the context of the recording as indicated by the presence or absence of the beacon signal.

The measurements may be flagged at flag operations 606 or 608 to simply indicate that a predefined patient context such as lying down is occurring while the measurements are being recorded. Alternatively, such as where multiple patient contexts may be detectable by providing IDs from the external devices 202 (i.e., bedside vs. car), the ID or other patient context descriptor may be logged in association with the physiological measurements being made. Subsequently, a physician or machine reviewing the measurements may account for the patient context that occurred, such as by applying a known correction factor to the measurements for the known patient context to normalize the measurements relative to a baseline context.

Figure 7:
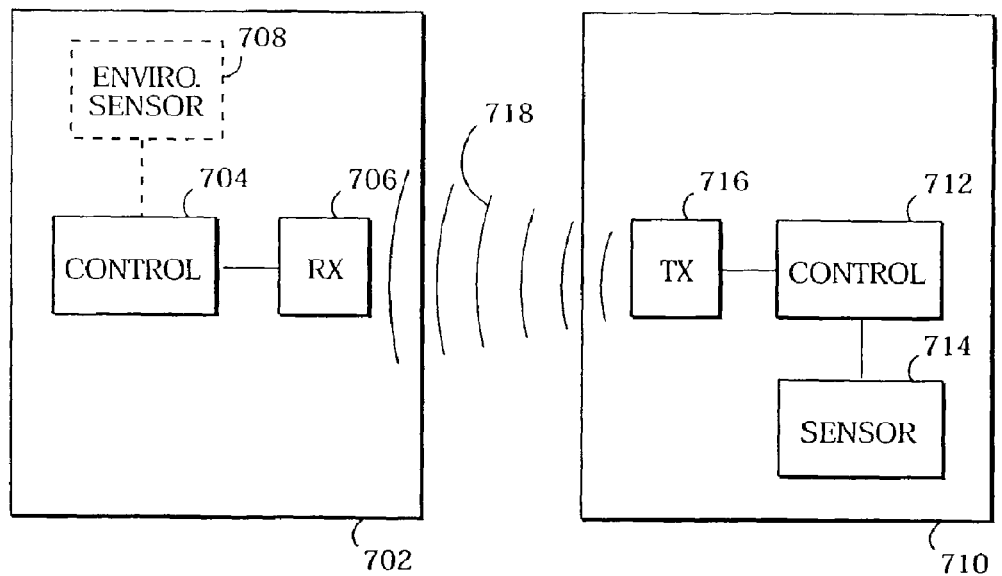
FIG. 7 is a block diagram of the major components of embodiments of devices of a second illustrative system for detecting context when measuring physiological conditions of the patient and/or providing a mode of therapy through proximity sensing.

FIG. 7 shows another illustrative system for detecting context when measuring a physiological condition or applying a mode of therapy by providing the beacon signal from the measurement device 710 rather than the external device 702. The system of FIG. 7 employs a measurement device 710 that includes a transmitter 716 coupled to a controller 712 that is also coupled to a sensor 714. The controller 712 receives the measurements from the sensor 714 and passes the measurements either continuously or periodically to the transmitter 716. The transmitter either continuously or periodically outputs a signal 718 encoded with the measurement data. Because battery life is typically of concern for a medical device coupled to a patient, intermittent transmissions from the transmitter 716 may be appropriate for a particular situation to reduce the drain on the power source for the measurement device 710.

The signal 718 is received by a receiver 706 of an external device 702 when the device 702 is within transmission range of the measurement device 710 while the transmitter 716 is providing the signal 718. A controller 704 of the device 702 acts as a data logger to store the data in memory or forward that data on to another device or network. The controller 704 may be configured to respond to receiving the signal from the transmitter 716 by beginning the recording of the data as soon as the receiver 706 is in range. Alternatively, the controller 704 may be configured to begin recording data, flagging data, or logging the patient context only upon an indication within the signal 718 that a particular patient context has been detected by the measurement device. For example, an incorporated tilt switch may indicate that the patient is recumbent, and this indication is provided through the signal 718 to the controller 704 to control how and whether the measurement data of the signal 718 is recorded.

As another alternative, transmission from the measurement device 710 may be controlled in other ways based upon patient context determined by a device coupled to the patient, such as a tilt switch in communication with the controller 712. For example, the transmission of signal 718 may occur only during periods when the patient is recumbent. So, the system of FIG. 7 may be configured so that recording of the physiological measurements occurs at the device 702 only when the devices are in proximity and the patient is recumbent. Additional contextual conditions may be imposed as well, such as recording the data only when the environmental sensor 708 has a certain output or the environmental measurement may be logged with the measurement data being recorded.

Furthermore, the controller 704 may make a determination as to what mode of therapy should be provided based on whether the signal 718 is being received. In this scenario, the device 702 must have access to a transmitter and a device coupled to the patient 100 must include a receiver such that the controller 704 may convey instructions to the device coupled to the patient 100 to initiate execution of a particular mode of therapy.

Figure 8:
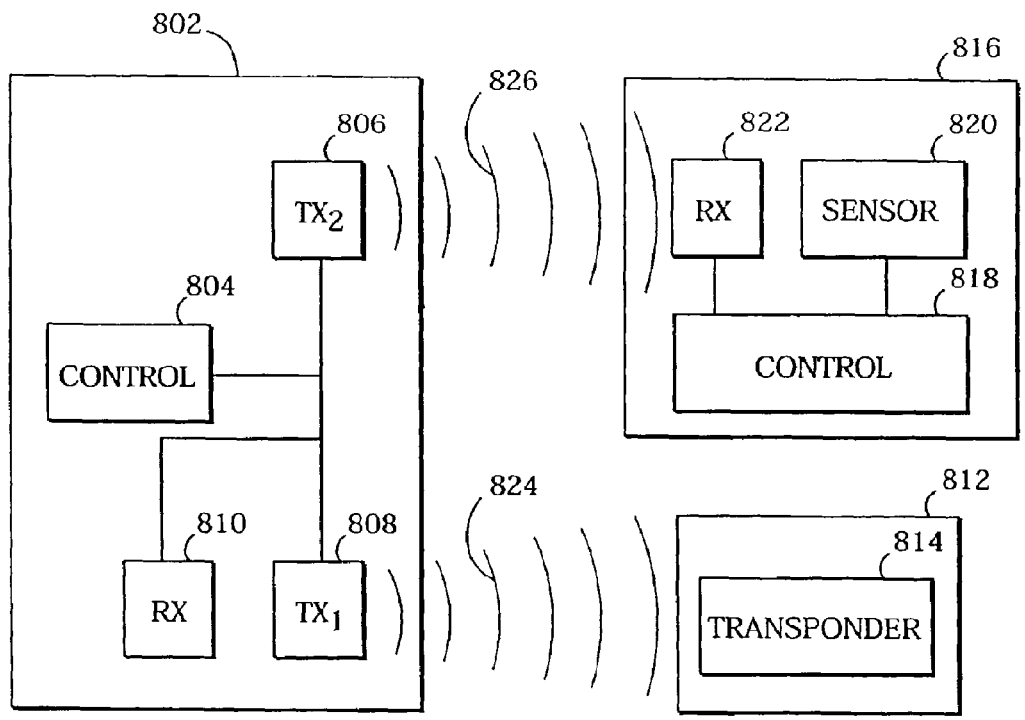
FIG. 8 is a block diagram of the major components of embodiments of devices of a third illustrative system for detecting context when measuring physiological conditions of the patient and/or providing a mode of therapy through proximity sensing.

FIG. 8 shows another illustrative system to detect a patient context through proximity sensing that utilizes an external device 802 that communicates with a first assembly 812 coupled to the patient 100 that includes a transponder chip 814. For example, the first assembly 812 may be a bracelet or other jewelry worn by the patient 100 that includes the transponder chip 812. The transponder chip 814 is responsive to an electromagnetic wave by reflecting the wave with an ID encoded in the reflection.

An external device 802 includes a transmitter 808 that transmits an electromagnetic wave 824 that may be reflected by the transponder chip 814 when the transponder chip 814 is within range of the external device 802. A receiver 810 included in the external device 802 receives the reflected electromagnetic wave from the transponder chip 814 and provides the ID of the reflected wave to a controller 804. Thus, the range of the transponder chip 814 for receiving and reflecting an electromagnetic wave defines the area of proximity that is used to detect a patient context such as lying down or driving. The controller 804 then causes a second transmitter 806 to transmit a signal 826 to a measurement device 816 upon receiving the reflected wave from the transponder chip 814.

The measurement device 816 is coupled to the patient 100, either externally or as an implant. The measurement device 816 includes a controller 818 coupled to a receiver 822 and a sensor 820. The receiver 822 receives the signal 826 transmitted by the external device 802. Upon receiving the signal 826, a controller 818 coupled to the receiver 822 begins recording physiological measurements made by a sensor 820, flagging measurements already being made, or logs a patient context with the measurements. As discussed above in relation to other illustrative systems, the controller 818 may transmit the measurement and context information to additional devices if the measurement device 816 is equipped with a transmitter. Additionally or alternatively, the controller 818 may activate a mode of therapy depending upon whether the signal 826 is being received.

Figure 9:
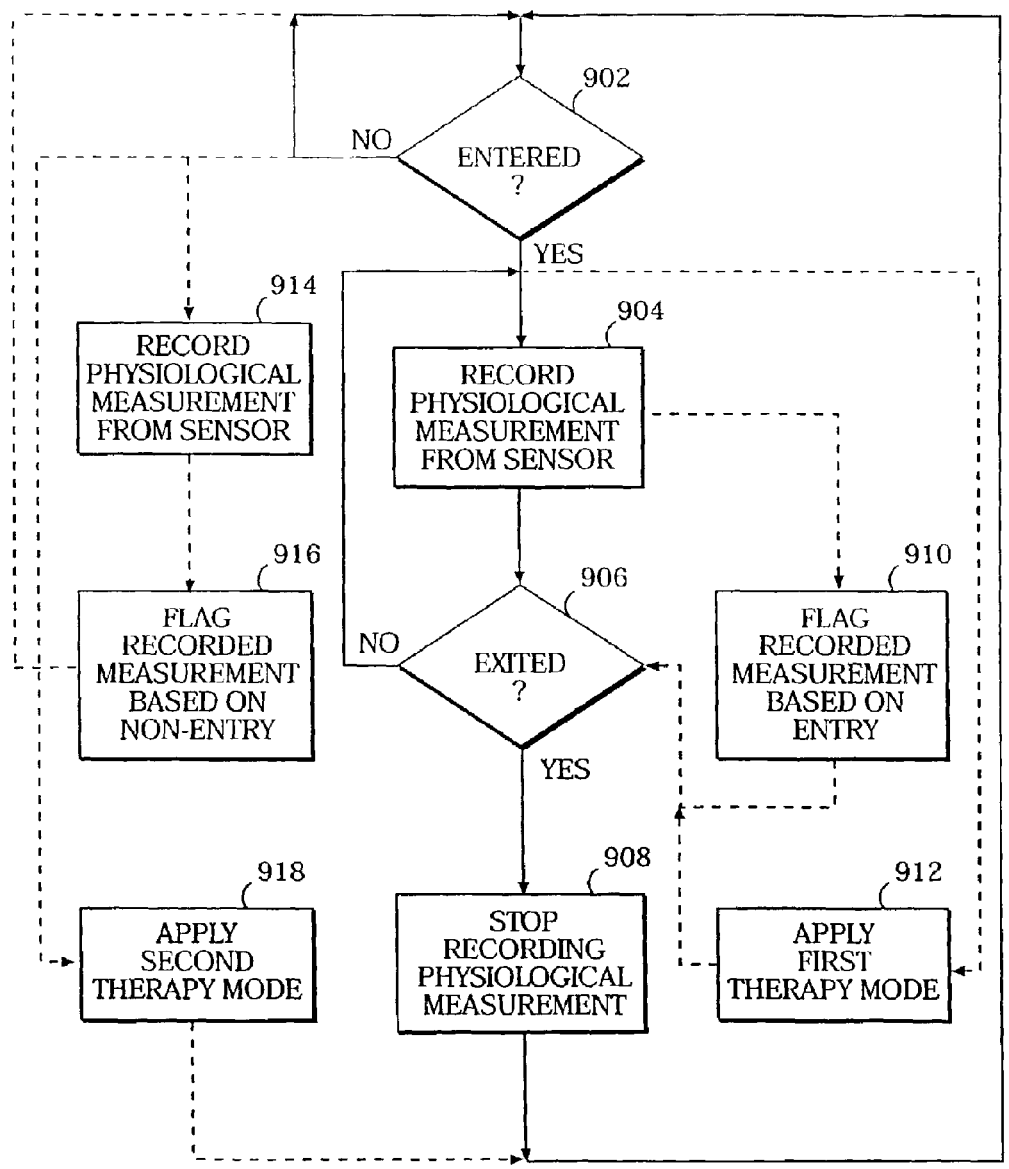
FIG. 9 shows an additional embodiment of the logical operations of an illustrative system for detecting patient context when measuring physiological conditions and/or when providing a first or second mode of therapy through monitoring ingress and egress.

FIG. 9 shows the logical operations of another system for detecting context in relation to physiological conditions of a patient. The logical operations of FIG. 9 provide monitoring of ingress and egress from a particular location that is associated with a known patient context. For example, it may be utilized to detect that a patient is entering or exiting a room used for exercise where exercise is a patient context that results in measurements to be recorded or ignored or where exercise dictates a particular mode of therapy to be employed. A system such as that shown in FIG. 3 is appropriate where an external device such as device 202 transmits one or more beacon signals at the doorway. As the patient 100 enters or exits through the doorway, the measurement device 102 momentarily receives the beacon signal(s). Rather than measuring, or not measuring, during the period when the beacon signal(s) is in range, the measurement device 102 begins recording upon momentarily receiving the signal at one time and stops measuring upon momentarily receiving the signal at another time. Likewise, the device 102 may initiate a first therapy mode upon receiving the signal(s) at one time and then initiate a second mode of therapy upon receiving the signal(s) at a subsequent time.

The logical operations of the controller of the measurement device 102 for this system begin at query operation 902 where the controller detects whether the patient has entered (or exited) the room by determining if the receiver has momentarily received the beacon signal for the first time. As an alternative, multiple beacons may be provided at the doorway so that the beacons are received in one sequence upon ingress and are received in the reverse order upon egress and the device 102 can then determine whether the patient 100 is entering or exiting. If the beacon signals are not received, then query operation 902 repeats until the reception of the beacon signal has occurred. Alternatively, the controller may begin to record the physiological measurement from the sensor at record operation 914 and then flag the recorded measurements with an indicator based on the patient's non-entry at flag operation 916. As another alternative, the controller may initiate or continue the application of a second therapy mode at therapy operation 918.

Once query operation 902 detects that the beacon signal has been received, the controller begins recording the physiological measurements of the sensor, logging the patient context with the measurements being recorded, or applying a correction factor to the measurements at record operation 904. Additionally or alternatively, the controller begins flagging the measurements with an indicator based on the patient's entry at flag operation 910. Additionally or alternatively, the controller initiates application of a first mode of therapy at therapy operation 912.

During this time, the controller again detects whether the beacon signal has been momentarily received again at query operation 906. If not, then the controller continues to correlate the physiological measurements with the context as was started at record operation 904 and/or flag operation 906 or continues to apply the first mode of therapy. Once query operation 906 detects that the receiver has received the beacon signal again or in the order of egress for a multi-beacon setup, then the controller stops correlating the physiological measurements with the patient context defined by the entry (or exit) to the room at stop operation 908. Stopping correlation of the measurements with the context may involve stopping the recording of measurements altogether, stopping the flagging of measurements being recorded, stopping or changing the patient context being logged in association with the measurements being recorded, or stopping or changing the correction factors applied to the measurements. Furthermore, after exiting, query operation 902 will detect that the patient has not re-entered so that the second therapy mode will be initiated by the controller at therapy operation 918.

The controller of the various devices discussed herein may be of various forms of a processing device for implementing the logical operations also discussed above. For example, the controller may be hardwired digital logic such as an application specific integrated circuit. As another example, the controller may be a general-purpose programmable processing device implementing code stored in memory.

While the invention has been particularly shown and described with reference to illustrative embodiments thereof, it will be understood by those skilled in the art that various other changes in the form and details may be made therein without departing from the spirit and scope of the invention.

What is claimed is:

1. A system for monitoring physiological conditions of an ambulatory patient capable of moving among a plurality of environmental locations external to the patient based on a detection of at least one posture associated with the patient, the system comprising:
   a detector, including a first device positioned in one of the plurality of environmental locations and a second device attached to the ambulatory patient, the first and second devices configured to cooperate to detect the patient being within a specified range of the first device and to determine the at least one posture associated with the patient in response to the patient being within the specified range of the first device;
   a physiological sensor that is responsive to a physiological condition of the patient; and
   a processing device configured to automatically measure from the physiological sensor at least one physiological condition of the patient in response to the detection of the at least one posture.

2. The system of claim 1 further comprising a transmitter that outputs a signal encoded with the measurements made by the processing device from the physiological sensor.

3. The system of claim 1, wherein the processing device is configured to flag the measurements taken in response to the detection of the at least one posture.

4. The system of claim 1, wherein the physiological sensor comprises a pulse rate sensor.

5. The system of claim 1, wherein the processing device is configured to record measurements of the physiological condition in response to the detection of a predefined patient posture.

6. The system of claim 1, wherein the processing device is configured to store the measurements of the physiological condition in association with the at least one detected posture.

7. The system of claim 1, wherein the processing device is configured to correct the measurements of the at least one physiological condition by application of a correction factor associated with the detected at least one posture.

8. The system of claim 1, wherein the detector comprises at least one transmitter external to the patient and a receiver responsive to the transmitter.

9. The system of claim 8, wherein the receiver is implantable.

10. The system of claim 1, wherein the detector comprises a transmitter external to the patient and a transponder responsive to the transmitter.

11. The system of claim 1, wherein the detector comprises multiple transmitters external to the patient and a receiver responsive to the transmitters, wherein the transmitters transmit data regarding multiple contexts.

12. A system for monitoring physiological conditions of an ambulatory patient capable of moving among a plurality of environmental locations external to the patient, the system comprising:
- a detector including a first device positioned in one of the plurality of environmental locations and a second device attached to the ambulatory patient, the first and second devices configured to cooperate to detect the patient being within a specified range of the first device and to determine at least one posture associated with the patient in response to the patient being within the specified range of the first device;
- a physiological sensor that is responsive to a physiological condition of the patient; and
- a processing device that is configured, in response to the detection of the at least one posture, to:
  - automatically perform measurements from the physiological sensor of at least one physiological condition of the patient;
  - flag the measurements; and
  - record the measurements.

13. The system of claim 12, wherein the processing device is configured to store the measurements in response to the detection of a predefined patient posture.

14. The system of claim 12, wherein the physiological sensor comprises a pulse rate sensor.

15. The system of claim 12, wherein the processing device is configured to correct the measurements of the at least one physiological condition by application of a correction factor associated with the detected at least one posture.

16. A system for monitoring physiological conditions of an ambulatory patient capable of moving among a plurality of environmental locations external to the patient, the system comprising:
- a detector, including a first device positioned in one of the plurality of environmental locations and a second device attached to the ambulatory patient, the first and second devices configured to cooperate to detect the patient being within a specified range of the first device and to determine at least one posture associated with the patient in response to the patient being within the specified range of the first device;
- a physiological sensor that is responsive to a physiological condition of the patient;
- a processing device configured to automatically perform measurements from the physiological sensor of at least one physiological condition of the patient in response to the detection of the at least one posture;
- a transmitter configured to output the measurements of the at least one physiological condition; and
- a receiver that is responsive to the transmitter.

17. The system of claim 16, wherein the transmitter is external to the patient.

18. The system of claim 16, wherein the transmitter is configured to output a signal encoded with the measurements made by the processing device from the physiological sensor.

19. The system of claim 16, wherein the transmitter is configured to transmit data regarding multiple contexts.

20. The system of claim 16, wherein the transmitter is configured to transmit data regarding at least on of a patient context or an environmental context.

* * * * *